(12) United States Patent
Saerens et al.

(10) Patent No.: US 11,134,700 B2
(45) Date of Patent: Oct. 5, 2021

(54) **ENHANCEMENT OF COCOA QUALITY AND FLAVOR BY USING *PICHIA KLUYVERI* YEAST STARTER CULTURE FOR COCOA FERMENTATION**

(71) Applicant: Chr. Hansen A/S, Hørsholm (DK)

(72) Inventors: Sofie Saerens, Skovlunde (DK); Jan Hendrik Swiegers, Fredensborg (DK)

(73) Assignee: CHR. HANSEN A/S, Hoersholm (DK)

( * ) Notice: Subject to any disclaimer, the term of this patent is extended or adjusted under 35 U.S.C. 154(b) by 652 days.

(21) Appl. No.: 15/654,372

(22) Filed: Jul. 19, 2017

(65) Prior Publication Data
US 2017/0311620 A1    Nov. 2, 2017

Related U.S. Application Data

(62) Division of application No. 14/355,807, filed as application No. PCT/EP2012/071787 on Nov. 5, 2012, now abandoned.

(30) Foreign Application Priority Data

Nov. 3, 2011   (EP) ........................................ 1187613

(51) Int. Cl.
| | | |
|---|---|---|
| A23G 1/30 | (2006.01) | |
| A23G 1/00 | (2006.01) | |
| A23G 1/42 | (2006.01) | |
| C12N 1/16 | (2006.01) | |
| A23G 1/02 | (2006.01) | |
| C12R 1/84 | (2006.01) | |

(52) U.S. Cl.
CPC ............... *A23G 1/30* (2013.01); *A23G 1/002* (2013.01); *A23G 1/02* (2013.01); *A23G 1/42* (2013.01); *C12N 1/165* (2021.05); *C12R 2001/84* (2021.05)

(58) Field of Classification Search
CPC . A23G 1/30; A23G 1/002; A23G 1/42; A23G 1/02; C12N 1/165
USPC .......................................................... 426/45
See application file for complete search history.

(56) References Cited

U.S. PATENT DOCUMENTS

2014/0271989 A1    9/2014   Saerens et al.

FOREIGN PATENT DOCUMENTS

| WO | WO-2007/031186 A1 | 3/2007 | |
|---|---|---|---|
| WO | WO-2009/103137 A2 | 8/2009 | |
| WO | WO2009103137 * | 8/2009 | ............... A23G 1/02 |

(Continued)

OTHER PUBLICATIONS

Masoud, W. et al. 2006. Int. J. Microbiol. 110: 291-296 (Year: 2006).*

(Continued)

*Primary Examiner* — Hamid R Badr
(74) *Attorney, Agent, or Firm* — Foley & Lardner LLP (57) ABSTRACT

Described are *Pichia kluyveri* yeast strains with advantageous properties useful in cacao fermentation processes, and related methods and products, including fermented cocoa beans having a ratio of isobutyl acetate/isobutanol higher than 1 and/or a ratio of isoamyl acetate/isoamyl alcohol higher than 0.005, and cocoa-based products prepared therefrom, as well as methods for the fermentation of cocoa beans comprising using at least one *Pichia kluyveri* yeast strain, fermented cocoa beans obtainable thereby, and cocoa-based products prepared therefrom and obtainable thereby.

16 Claims, 9 Drawing Sheets

(56) References Cited

FOREIGN PATENT DOCUMENTS

WO     WO-2011/012680 A2     2/2011

OTHER PUBLICATIONS

Buzzini, P. et al. Antonie van Leeuwenhoek . 2003. 84: 301-311 (Year: 2003).*

Rodriguez-Campos, J. et al. Food Res. Int. 2011.44: 250-258 (Year: 2011).*

Afoakwa, et al. "Flavor Formation and Character in Cocoa and Chocolate: A Critical Review". Critical Reviews in Food Science and Nutrition, 2008, vol. 48, No. 9, pp. 840-857.

Biehl, et al. "Acidification, Proteolysis and Flavour Potential in Fermenting Cocoa Beans", Journal of the Science of Food and Agriculture, Jan. 1, 1985, vol. 36, No. 7, pp. 583-598.

Buamah, et al. "Pure yeast culture fermentation of cocoa (*Therobroma cacao* L): effect on yield of sweating and cocoa bean quality", World Journal of Microbiology & Biotechnology, Jan. 1997, vol. 13, pp. 457-462.

International Search Report dated Feb. 11, 2013 issued in connection with International Application No. PCT/EP2012/071787.

Jespersen, "Occurrence and taxonomic characteristics of strains of *Saccharomyces cerevsiae* predominant in African indigenous fermented foods and beverages", FEMS Yeast Research, 2003, vol. 3, pp. 191-200 (published online Oct. 2002).

Jespersen, et al. "Occurrence and diversity of yeasts involved in fermentation of West African cocoa beans", FEMS Yeast Research, Feb. 2005, vol. 5, pp. 441-453 (published online Dec. 2004).

Leal, Jr., et al. "Fermentation of cacao (*Theobroma cacao* L.) seeds with a hybrid Kluyveromyces marxianus strain improved product quality attributes", FEMS Yeast Research, 2008, vol. 8, pp. 788-798 (published online Jul. 2008).

Lefeber, et al. "Kinetic Analysis of Strains of Lactic Acid Bacteria and Acetic Acid Bacteria in Cocoa Pulp Simulation Media toward Development of a Starter Culture of Cocoa Bean Fermentation", Applied and Environmental Microbiology, Dec. 2010, vol. 76, No. 23, pp. 7708-7716.

Lefeber, et al. "Simulated Cocoa Pulp Fermentations of CoCoa-Specific Lactic Acid Bacteria Reveal Interesting Starter Culture Strains for Controlled Cocoa Bean Fermentation", AEM Accepts, (published online Jul. 29, 2011).

Lima, et al. "*Theobroma cacao* L., "The Food of the Gods"; Quality Determinants of Commercial Cocoa Beans, with Particular Reference to the Impact of Fermentation", Critical Reviews in Food Science and Nutrition, 2011, vol. 51, No. 8, pp. 731-761 (published online May 2011).

Schwan, "Cocoa Fermentations Conducted with a Definied Microbial Cocktall Inoculum", Applied and Environmental Microbiology, Apr. 1998, vol. 64, No. 4, pp. 1477-1483.

Schwan, et al. "The Microbiology of Cocoa Fermentation and its Role in Chocolate Quality", Critical Reviews in Food Science and Nutrition, Jul. 2004, vol. 44, No. 4, pp. 205-211.

Advisory Action issued in U.S. Appl. No. 14/355,807, dated Jul. 17, 2017.

Final Office Action issued in U.S. Appl. No. 14/355,807, dated Apr. 19, 2017.

Non-Final Office Action issued in U.S. Appl. No. 14/355,807, dated Dec. 1, 2016.

Rodriguez, et al., "Dynamics of volatile and non-volatile compounds in cocoa (*Theobroma cacao* l.) during fermentation and drying processes using principal components analysis," *Food Res. International*, vol. 44, pp. 250-258 (2011).

Advisory Action issued in U.S. Appl. No. 14/355,807, dated Aug. 17, 2016.

Final Office Action issued in U.S. Appl. No. 14/355,807, dated Jun. 9, 2016.

Praag et al., "Steam Volatile Aroma Constitutents of Roasted Cocoa Beans," *J. Agr. Food Chem.*, vol. 16, pp. 1005-1008 (1968).

Booth et al., "Hydrotropic Solubilities, Solubilities in 40 Per Cent Sodium Xylenesulfonate," *Indust. Eng. Chem.*, vol. 40, pp. 1491-1493 (1948).

Non-Final Office Action issued in U.S. Appl. No. 14/355,807, dated Nov. 23, 2015.

Jinap, et al., "Effect of Roasting Time and Temperature on Volatile Component Profiles during Nib Roasting of Cocoa beans (*Theobroma cacao*)," *J. Sci. Food Agric.*, vol. 77, pp. 441-448 (1998).

Restriction Requirement issued in U.S. Appl. No. 14/355,807, dated Jul. 14, 2015.

Zorg, et al., "Killer toxin producing strains of the yeasts *Hanseniaspora uvarum* and *Pichia kluyveri*," *Arch. Microbiol.*, vol. 149, pp. 261-267 (1988).

Oberparleiter et al., "Amyl alcohols as compounds indicative of raw cocoa bean quality," *Z. Lebensum Forsh A*, vol. 204, pp. 156-160 (1997).

Rodriguez-Campos et al., "Effect of fermentation time and drying temperature on volatile compounds in cocoa," *Food Chemistry*, vol. 132, pp. 277-288 (2012).

Non-English Thesis by Denise Sande Santos entitled "Inoculation of Starter Yeasts in the Fermentation of Cocoa to Improve Flavor," 93 pages (2010).

Partial English Translation of Thesis by Denise Sande Santos entitled "Inoculation of Starter Yeasts in the Fermentation of Cocoa to Improve Flavor," 27 pages (2010).

* cited by examiner

ENHANCEMENT OF COCOA QUALITY AND FLAVOR BY USING *PICHIA KLUYVERI* YEAST STARTER CULTURE FOR COCOA FERMENTATION

CROSS REFERENCE TO RELATED APPLICATIONS

The present application is a divisional of U.S. patent application Ser. No. 14/355,807, which was the U.S. National Stage of International Application No. PCT/EP2012/071787, filed Nov. 5, 2012, which claims the benefit of European Patent Application No. 11187613.2, filed Nov. 3, 2011.

FIELD OF THE INVENTION

The present invention relates to the field of cocoa fermentation. Specifically, the invention relates to a method of fermenting cocoa material, such as cocoa beans and pulp, with a *Pichia kluyveri* yeast strain.

BACKGROUND OF THE INVENTION

The quality of commercial cocoa beans, the principal raw material for chocolate production, relies on the combination of factors that include the type of plant material, the agricultural practices, and the post-harvest processing. Among these, the fermentation of the cocoa beans is the most relevant since it is the process whereby the precursors of the cocoa flavor arise. The formation of these precursors depends on the activity of different microbial species on the pulp surrounding the beans.

From the 22 species that constitute the genus *Theobroma* (family Sterculiaceae), *Theobroma cacao* L., is commercially the most important, due to the value of its seeds (Uma et al. 2011). There are three main botanical varieties of *Theobroma cacao*: Forastero, Criollo and Trinitario. Forastero populations, probably native to the Amazon basin, supply over 95% of the world's cocoa (ICCO, 2007). The seeds of this variety are flat, astringent, and purple in color due to the presence of anthocyanins. Forastero cocoa trees are very productive and are considered to be moderately resistant to pests (Uma et al. 2011). Criollo is the original cultivated variety, indigenous to Northern, Southern and Central America. The beans are white to ivory or have very pale purple color. The low yields and their susceptibility to many diseases make them rare to cultivate. The Trinitario type originated in Trinidad and covers all products of natural hybridization and recombination of the Criollo and Forastero varieties. The beans are variable in colour, although rarely white, and the trees show a susceptibility to pests and diseases intermediate to Forastero and Criollo varieties. Both the Trinitario and Criollo populations produce the 'fine' or 'flavor' cocoa beans, whose share in the total world production is below 5% (ICCO, 2007). These cocoa beans are used to make high quality dark chocolate.

The cocoa beans are the principal raw material for chocolate production. Not only is it not possible to make chocolate without cocoa beans, but also the distinctive flavor of chocolate is due to the presence of these beans. Other products derived from cocoa beans are cocoa powder, widely used in the food industry, and cocoa butter that in addition to its confectionery use also has cosmetic and pharmaceutical applications.

However, before cocoa beans can be traded and processed into final industrial products they have undergone post-harvest processing on farms and plantations comprising the steps of pod opening and beans removal from the pod, bean fermentation, and drying. In this sequence, the fermentation constitutes an essential critical step for the development of flavor quality attributes of the commercial cocoa beans. This is due to the fact that during the fermentation, biochemical transformations are induced within the beans leading to the formation of important precursors of the cocoa flavor, some of which are highly volatile compounds. The fermentation of the beans further causes browning, reduction of bitterness and astringency of the beans. The full cocoa flavor is developed later upon roasting, through complex reactions, mainly of the Maillard type (Afoakwa et al. 2008).

The fruit of the cocoa tree is botanically an indehiscent drupe, usually called pod. These are oval in shape, measure between 12 and 30 cm, and contain 30 to 40 beans embedded in a mucilaginous pulp, which comprises approximately 40% of the bean fresh weight (Schwan and Wheals, 2004). The pulp is characterized by a sugar content of around 9 to 13% (w/w), high acidity, conferred by the presence of diverse organic acids, but mainly citric acid, and a protein content in the range of 0.4 to 0.6% (w/w). The post-harvesting processing of the cocoa beans starts by breaking the pods and removing the seeds from the fruit for fermentation. The method for cocoa bean fermentation consists of piling a certain quantity of fresh beans in heaps, wooden boxes, trays or baskets and allowing naturally occurring microorganisms to develop (Schwan and Wheals, 2004). During this spontaneous fermentation, the beans are freed from adhering pulp and at the end of fermentation the decomposed pulp is generally washed away by water and the beans dried to produce the fermented cocoa beans of commerce.

The microbial activity in cocoa bean pulp is considered as a well-defined microbial succession led by yeasts that will dominate the total microbial population during the ten first hours of fermentation, after which their level is surpassed by those of lactic acid bacteria (LAB), that in turn decline after 48 h of fermentation in detriment of the vigorous development of acetic acid bacteria (AAB).

The metabolic activity of yeasts in the cocoa bean pulp leads to the production of ethanol, carbon dioxide, acids and volatile compounds, with a concomitant increase of temperature. Some yeasts are believed to metabolize citric acid (Jespersen 2003), which contributes to an increase in the pH value of the pulp. Moreover, yeasts have the ability to degrade the pulp by producing pectinolytic enzymes. Products of the metabolism of LAB include lactic acid, ethanol, acetic acid, and other organic acids, as well as glycerol, mannitol, carbon dioxide and volatiles. The production of the acids causes a drop in pH of the pulp, but the fact that yeasts can assimilate the lactic acid, together with the fermentative ability of LAB to use citric acid, partly explains why the overall effect of acids production may not produce such a pronounced drop in pH during the first two days of fermentation (Lima et al. 2011). The increase access of air in the cocoa bean mass resulting from the enzymatic collapse of the pulp stimulates the development of AAB, which convert the ethanol into acetic acid. Ethanol and acetic acid diffuse into the beans and together with the heat produced this causes the death of the seed embryo. This in turn initiates biochemical reactions in the beans leading finally to the development of a characteristic flavor and color of the beans. These properties are further developed during drying, roasting and final processing of the beans. In this way, the activity of yeasts, LAB and AAB is essential for the production of high-quality cocoa.

However, the spontaneous fermentation is very inhomogeneous and large variations occur in both microbial counts and species composition, even in fermentations occurring at the same site. The variations seem to depend on many factors including country, farm, pod ripeness, post-harvest pod handling, type of cocoa, fermentation method, size of the batch, turning or no turning, fermentation time etc. which makes it extremely difficult to control the cocoa fermentations and as a result the reproducibility of the fermentations is almost impossible. The core problem here seems to be the lack of control over the growth and development of microorganisms and metabolites produced during the fermentation process, which results in a variable quality of the finished cocoa beans.

Attempts have been made in the prior art to control the fermentation conditions of cocoa bean fermentations.

In literature, some papers refer to the use of starter cultures for cocoa bean fermentation. Schwann (1998) and Schwan and Wheals (2004) disclose the use of starter cultures in cocoa bean fermentation with an inoculum consisting of the strains *Saccharomyces cerevisiae* var. *chevalieri, Lactobacillus lactis, Lactobacillus plantarum, Acetobacter aceti* and *Gluconobacter oxydans*. Leal and coworkers (2008) disclose the single use of a hybrid *Kluyveromyces marxianus* with improved pectinolytic activity as a starter culture for cocoa bean fermentation. Finally, Lefeber and coworkers (2010 and 2011) disclose the use of specific lactic and acetic acid bacteria as ideal starter cultures for cocoa bean fermentation. However, Lefeber et al. only tested the bacteria in cocoa simulation medium.

International patent application WO 2007/031186 discloses a method to regulate the fermentation of plant material consisting of cocoa beans and/or cocoa pulp by adding to said plant material specific bacterial cultures containing at least one lactic acid bacterium and/or at least one acetic acid bacterium at different time points during the fermentation process.

International patent application WO 2011/012680 discloses a method to use a microbial composition for regulating the fermentation of cocoa material, such as cocoa beans and/or cocoa pulp, in particular using compositions comprising specific combinations of microorganisms including at least a *Lactobacillus plantarum, Lactobacillus fermentum* and an *Acetobacter pasteurianus*.

However, fermentation parameters remain difficult to control in prior art methods and better understanding of the biological processes that control the presence and amount of compounds in the fermentation of cocoa beans is highly desirable. Taste problems may still occur such as the presence of (too many) acids, a lack of cocoa taste and too much off-flavor. In particular, being able to regulate the amount and type of flavor compounds in cocoa beans would be very beneficial to cocoa producers. Regulation of the amount of esters and higher alcohols, and in particular isoamyl acetate, in combination with high quality beans would allow for the development of new technologies permitting the cocoa producers to obtain high quality cocoa beans with a different flavor profile. Such a technology would, therefore, be of significant commercial value.

Thus, there exists a need for improved processes for enhancement of desirable flavors in cocoa fermentation and for improvement of the quality of the fermented cocoa beans.

SUMMARY OF THE INVENTION

The problem to be solved by the present invention relates to the provision of a method for fermentation of cocoa beans and pulp wherein the presence of desirable flavor compounds, such as acetate esters, is enhanced and the overall quality of the fermentation is improved.

The solution is based on the surprising findings by the Inventors that by inoculation of the cocoa beans and pulp with a *Pichia kluyveri* yeast strain one is able to produce fermented cocoa beans with an improved flavor profile.

Accordingly, a first aspect of the present invention relates to fermented cocoa beans with an improved flavor profiles, such as fermented cocoa beans having a ratio of Isobutyl acetate/isobutanol higher than 1, such as higher than 1.2, and/or a ratio of Isoamyl acetate/isoamyl alcohol higher than 0.005, such as higher than 0.006.

A second aspect of the present invention relates to a cocoa-based product having an improved flavor profile, wherein the cocoa-based product is prepared from the fermented cocoa beans of the first aspect of the present invention.

A third aspect of the invention relates to a method for the fermentation of cocoa beans comprising the steps of:
  a) adding to a plant material essentially consisting of beans and/or pulp derived from fruit pods of the species *Theobroma cacao* at least one *Pichia kluyveri* yeast strain; and
  b) fermenting the plant material.

Preferably, the method for the fermentation of cocoa beans comprises the steps of:
  a) adding to a plant material essentially consisting of beans and/or pulp derived from fruit pods of the species *Theobroma cacao* at least one *Pichia kluyveri* yeast strain;
  b) fermenting the plant material; and
  c) drying the fermented cocoa beans.

A fourth aspect of the present invention relates to use of at least one *Pichia kluyveri* yeast strain for fermentation of cocoa beans to enhance flavor and/or the quality of the fermented beans.

A fifth aspect relates to a *Pichia kluyveri* yeast strain for use in fermentation of cocoa beans to enhance flavor and/or the quality of the fermented beans.

A sixth aspect of the present invention relates to fermented cocoa beans obtainable by the method according to the first aspect of the invention.

A seventh aspect of the present invention relates to a method for producing cocoa-based products comprising the steps of:
  a) providing cocoa beans that have been fermented with a method according to the first aspect of the present invention; and
  b) producing a cocoa-based product from the cocoa beans of step a).

An eighth aspect relates to cocoa-based products obtainable by the method according to the fourth aspect of the Invention.

DETAILED DESCRIPTION OF THE INVENTION

Definitions

The term "plant material" includes anything that is or was live vegetation, in particular plants and any parts thereof.

The term "fermentation" refers generally to any activity or process involving enzymatic decomposition (digestion) of organic materials by microorganisms. The term "fermentation" encompasses both anaerobic and aerobic processes, as well as processes involving a combination or succession of one or more anaerobic and/or aerobic stages. In the present invention, fermentation preferably involves the decomposition (digestion) of plant materials as defined above. "Fermentation" as used herein includes the oxidation of organic compounds such as the pulp.

A "spontaneous fermentation" as used herein is one that employs microorganisms naturally present in and/or unconsciously introduced into the fermented organic material at the start or during fermentation. Accordingly, in the above methods an otherwise spontaneous fermentation may be regulated by addition of at least one microbial strain as defined herein.

"Pulp" is the soft moist part of the fruit from a plant. Pulp of cocoa beans is sometimes referred to as "mucilage".

The term "cocoa bean" refers to the seed of any cocoa tree variety.

It is noted that the terms "cocoa" and "cacao" as used herein are considered as synonyms. The term "pod" refers to a mature or ripe cocoa fruit or seed case. As used in the present invention, the pod encloses the cocoa beans and the pulp.

The term "cocoa-based products" herein refers to products that are prepared using fermented cocoa beans. The products intend to refer to the products prepared starting from cocoa beans that have been subjected to fermentation as described herein. Cocoa-based products can be in a liquid form or In a dry or lyophilized form such as in the form of granules, pellets or a powder. As used herein "cocoa nib" refers to the fermented, dried cocoa bean without the shell.

The term "cocoa liquor" herein refers to ground cocoa nibs. Cocoa liquor is prepared by grinding roasted cocoa nibs into a dark paste. On cooling, cocoa liquor yields cocoa mass. When the nibs are ground up into a coarse uniform paste, they form what is known as "cocoa flakes". The term "cocoa flakes" thus refers to cocoa liquor in the form of solid flakes.

Cocoa liquor can be processed into two different components: cocoa powder and cocoa butter. The cocoa liquor is pressed into cocoa cake by removing most of the cocoa butter. The term "cocoa cake" thus refers to the cocoa solids or cocoa mass remaining after extraction of fat (cocoa butter) by pressing. Cocoa cakes can be broken up and ground into a fine cocoa powder. "Cocoa powder" refers to cocoa solids.

"Cocoa butter" is the fat component of chocolate liquor, whereas the remaining part of the chocolate liquor is cocoa solids or cocoa mass. For instance to produce dark chocolate, cocoa nibs or cocoa mass are mixed with sugar and sufficient cocoa butter to enable the chocolate to be molded. To produce milk chocolate, cocoa mass and cocoa butter are mixed with sugar and milk powder, while for white chocolate cocoa butter is mixed with sugar and milk powder.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or Improved, properties (e.g. regarding enhancement of desirable cocoa flavor compounds) as the mother strain. Such a mutant is a part of the present invention. Especially, the term "mutant" refers to a strain obtained by subjecting a strain of the Invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less than 5%, or less than 1% or even less than 0.1% of the nucleotides in the yeast genome have been shifted with another nucleotide, or deleted, compared to the mother strain.

In the present context, the term "variant" should be understood as a strain which is functionally equivalent to a strain of the invention, e.g. having substantially the same, or Improved, properties (e.g. regarding enhancement of desirable cocoa flavor compounds). Such variants, which may be identified using appropriate screening techniques, are a part of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "Including" and "containing" are to be construed as open-ended terms (i.e., meaning "Including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the Invention and does not pose a limitation on the scope of the Invention unless otherwise claimed. No language in the specification should be construed as indicating any non-claimed element as essential to the practice of the invention.

Implementation and Aspects of the Invention

The present invention is directed to at least one *Pichia kluyveri* yeast strain, and uses and methods for fermentation of cocoa plant material, including cocoa beans and cocoa pulp, with said at least one *Pichia kluyveri* yeast strain.

The present methods allow for controlling or manipulating the development of desirable characteristics, such as flavor compounds and other quality assets, such as extent of fermentation and characteristics of the fermented material, of the fermented cocoa beans and the cocoa-based products prepared there from.

In a first aspect the present invention relates to fermented cocoa beans having a ratio of isobutyl acetate/isobutanol higher than 1, such as higher than 1.2, and/or a ratio of isoamyl acetate/isoamyl alcohol higher than 0.005, such as higher than 0.006. Preferably, the fermented cocoa beans are of the variety Forastero.

The levels of isobutyl acetate, isobutanol, isoamyl acetate and Isoamyl alcohol may be determined by head-space gas chromatography couple with flame ionization detection as set out in Example 1 herein or by any other method known to the skilled person.

In a second aspect the present invention is related to a cocoa-based product having an improved flavor profile, wherein the cocoa-based product is prepared using fermented cocoa beans according to the first aspect of the present invention.

In a third aspect the present invention is related to a method for fermentation of cocoa beans comprising the steps:
 a) adding to a plant material essentially consisting of beans and/or pulp derived from fruit pods of the species *Theobroma cacao* at least one *Pichia kluyveri* yeast strain;
 b) fermenting the plant material; and
 c) drying the fermented cocoa beans.

The species *Theobroma cacao* as used herein comprises all varieties, particularly all commercially useful varieties, including but not limited to Forastero, Criollo, Trinitario, Arriba and crosses and hybrids thereof. Cocoa beans derived from the fruit pods of *Theobroma cacao* are the principal raw material for chocolate production. The cocoa beans are embedded in a mucilaginous pulp inside the pods. After the pods are harvested, the cocoa beans (usually including at least a portion of the surrounding pulp) are recovered from the pods. Accordingly, the plant material used in the method of the Invention may preferably comprise cocoa beans derived from the fruit pods of *Theobroma cacao*, and may further comprise the pulp derived from said fruit pods.

The at least one *Pichia kluyveri* strain may be in frozen, liquid or dried form, including e.g. freeze dried form and spray/fluid bed dried form, or frozen or freeze-dried concentrates.

In a preferred embodiment the *Pichia kluyveri* strain is selected from the group consisting of *Pichia kluyveri* strain PK-KR1 and *Pichia kluyveri* strain PK-KR2 deposited at the National Measurement Institute, 541-65 Clarke Street, South Melbourne, Victoria 3205, Australia, by University of Auckland, School of Biological Sciences, Auckland 1142, New Zealand, and given the accession numbers V06/022711 and V06/022712, respectively, and mutant and variant strains thereof, wherein the mutant and variant strains thereof have retained or further improved the flavoring properties of V06/022711 and V06/022712, respectively.

Preferably, step a) is carried out at the start of fermentation.

In a preferred embodiment the plant material is fermented with the at least one *Pichia kluyveri* strain for at least 12 hours, such as for at least 24 hours, such as for at least 2 days, such as for at least 3 days, such as for at least 4 days, such as for at least 5 days, such as for at least 6 days, such as for at least 7 days.

The fermentation in preferred embodiments is carried out in heaps, wooden boxes, trays or baskets to allow for spontaneous fermentation to occur.

In a preferred embodiment the method for fermentation of cocoa beans further comprises adding to the plant material at least one lactic acid bacterial strain. In a more preferred embodiment, the at least one lactic acid bacterial strain is a *Lactobacillus plantarum* bacterial strain. In another more preferred embodiment the at least one lactic acid bacterial strain is a *Lactobacillus paracasei* bacterial strain.

Preferably, the at least one lactic acid bacterial strain is added at least 12 hours, such as at least 24 hours, such as at least 36 hours, such as at least 48 hours, after the addition of the first composition comprising at least one *Pichia kluyveri* strain.

In an embodiment of the present invention the at least one *Pichia kluyveri* strain is added to the plant material as a first starter culture. The term "starter culture" refers to a composition comprising live microorganisms that are capable of Initiating or effecting fermentation of organic material, optionally after being cultivated in a separate starter medium for obtaining a high density culture. Accordingly, in an embodiment, a starter culture of the invention may be a high density culture obtained by propagating a starter culture in a suitable medium.

A starter culture according to the present invention may also contain in addition to microorganisms, buffering agents and growth stimulating nutrients or preservatives or other carriers, such as milk powder or sugars.

In a preferred embodiment the first starter culture contains at least $10^2$ colony forming units (CFU)/g of *Pichia kluyveri* yeast strain, such as at least $10^3$ CFU/g, such as at least $10^4$ CFU/g, such as at least $10^5$ CFU/g, such as at least $10^6$ CFU/g, such as at least $10^7$ CFU/g, such as at least $10^6$ CFU/g, such as at least $10^9$ CFU/g, such as at least $10^{10}$ CFU/g, such as at least $10^{11}$ CFU/g, such as at least $10^{12}$ CFU/g, such as at least $10^{13}$ CFU/g.

In another preferred embodiment the first starter culture contains between $10^2$ and $10^{10}$ CFU/g of the plant material of *Pichia kluyveri* yeast strain, such as between $10^3$ and $10^9$ CFU/g, such as between $10^4$ and $10^8$ CFU/g, such as between $10^5$ and $10^7$ CFU/g.

In yet another embodiment of the present invention the at least one lactic acid bacterial strain is added to the plant material as a second starter culture.

A starter culture according to the present invention may also contain in addition to microorganisms, buffering agents and growth stimulating nutrients or preservatives or other carriers, such as milk powder or sugars.

In a preferred embodiment the second starter culture contains at least $10^2$ colony forming units (CFU)/g of lactic acid bacterial strain, such as at least $10^3$ CFU/g, such as at least $10^4$ CFU/g, such as at least $10^5$ CFU/g, such as at least $10^6$ CFU/g, such as at least $10^7$ CFU/g, such as at least $10^8$ CFU/g, such as at least $10^9$ CFU/g, such as at least $10^{10}$ CFU/g, such as at least $10^{11}$ CFU/g, such as at least $10^{12}$ CFU/g, such as at least $10^{13}$ CFU/g.

In another preferred embodiment the second starter culture contains between $10^2$ and $10^{12}$ CFU/g of the plant material of lactic acid bacterial strain, such as between $10^3$ and $10^{11}$ CFU/g, such as between $10^4$ and $10^{10}$ CFU/g, such as between $10^5$ and $10^9$ CFU/g.

A fourth aspect of the invention relates to the use of at least one *Pichia kluyveri* yeast strain for fermentation of cocoa beans to enhance the flavor and/or the quality of the fermented beans.

In a preferred embodiment the use of at least one *Pichia kluyveri* yeast strain for fermentation of cocoa beans and/or pulp is to enhance the flavor by increasing the ratio of isobutyl acetate/isobutanol to higher than 1, such as higher than 1.2, and/or the ratio of isoamyl acetate/Isoamyl alcohol to higher than 0.005, such as higher than 0.006, after fermentation of cocoa beans and/or pulp for 7 days at 30° C. followed by drying at 40° C. for 7 days and/or the quality of the fermented beans by increasing the amount of liquefied pulp to higher than 95% after fermentation of cocoa beans and/or pulp for 7 days at 30° C.

In a much preferred embodiment the *Pichia kluyveri* strain is selected from the group consisting of *Pichia kluyveri* strain PK-KR1 and *Pichia kluyveri* strain PK-KR2 deposited at the National Measurement Institute, 541-65 Clarke Street, South Melbourne, Victoria 3205, Australia, by University of Auckland, School of Biological Sciences, Auckland 1142, New Zealand, and given the accession numbers V06/022711 and V06/022712, respectively, and mutants and variants thereof, wherein the mutant and variant strains thereof have retained or further improved the flavoring properties of V06/022711 and V06/022712, respectively.

A fifth aspect of the invention relates to a *Pichia kluyveri* yeast strain for use in fermentation of cocoa beans to enhance the flavor and/or the quality of the fermented beans.

In a preferred embodiment the *Pichia kluyveri* yeast strain for use in fermentation of cocoa beans and/or pulp enhances the flavor by increasing the ratio of Isobutyl acetate/isobutanol to higher than 1, such as higher than 1.2, and/or the ratio of isoamyl acetate/isoamyl alcohol to higher than 0.005, such as higher than 0.006, after fermentation of cocoa beans and/or pulp for 7 days at 30° C. followed by drying at 40° C. for 7 days and/or the quality of the fermented beans by increasing the amount of liquefied pulp to higher than 95% after fermentation of cocoa beans and/or pulp for 7 days at 30° C.

In a much preferred embodiment the *Pichia kluyveri* strain is selected from the group consisting of *Pichia kluyveri* strain PK-KR1 and *Pichia kluyveri* strain PK-KR2 deposited at the National Measurement Institute, 541-65 Clarke Street, South Melbourne, Victoria 3205, Australia, by University of Auckland, School of Biological Sciences, Auckland 1142, New Zealand, and given the accession numbers V06/022711 and V06/022712, respectively, and mutants and variants thereof, wherein the mutant and variant strains thereof have retained or further improved the flavoring properties of V06/022711 and V06/022712, respectively.

A sixth aspect of the present invention relates to fermented cocoa beans obtainable by carrying out the method according to the first aspect of the Invention.

In a seventh aspect the present invention provides a method for producing cocoa-based products comprising the steps of:

c) providing cocoa beans that have been fermented with a method according to the first aspect of the present invention; and d) producing a cocoa-based product from the cocoa beans of step a).

In a preferred embodiment the cocoa-based products include cocoa nibs, cocoa flakes, cocoa cake, cocoa powder, cocoa liquor and chocolate including dark chocolate, milk chocolate or white chocolate.

In an eighth aspect the present invention relates to a cocoa-based product obtainable by carrying out the method of the fourth aspect of the invention.

EXAMPLES

Example 1

Materials and Methods
Fermentation Set-Up

Lab-scale cacao fermentation trials were carried out with 250 g of fresh cocoa beans (Forastero variety). The cocoa beans were retrieved from Ghana. The cocoa beans were collected in 500 ml glass bottles, which were loosely closed with a cap. Fermentation was carried out at 30° C. for 7 days. 7 different yeast stains were inoculated on the cocoa beans at 5 million CFU/g of cocoa beans: *Saccharomyces cerevisiae, Pichia kluyveri* PK-KR1, *Torulaspora delbrueckii, Kluyveromyces thermotolerans, Candida krusei, Hanseniapora guillermondii* and *Pichia membranifaciens*. After fermentation, the fermented cocoa beans were artificially dried in an oven at 40° C. for up to 7 days.

Headspace GC-FID Analysis

Headspace gas chromatography coupled with flame ionisation detection (GC-FID) was used for the measurement of acetaldehyde, acetate esters, ethyl esters and higher alcohols in the fermentation products.

Per yeast fermentation 6 fermented and dried cocoa beans were analyzed for their flavor profile. The beans were broken open and the outer layer was removed. The inside of the bean (nibs) was crushed to small pieces and collected in vials. Samples were then analyzed with a calibrated Perkin Elmer GC System with a headspace sampler. The GC was equipped with a DB-WAXETR column (length, 30 m; internal diameter, 0.25 mm; layer thickness, 0.5 µm; Agilent Technologies, Germany). The split-splitless injector was used and held at 180° C. Samples were heated for 30 min at 70° C. in the headspace autosampler before injection (needle temperature: 110° C.). Helium was used as the carrier gas. After starting at 60° C., the oven temperature was raised after 2 min from 60° C. to 230° C. at 45° C./min and was finally held at 230° C. for 5 min. During the GC-program a constant flow rate (10 ml/min) of the carrier gas (He) was maintained. The FID temperature was kept constant at 220° C. respectively. The results were analyzed with Turbochrom software.

Results

Lab-scale fermentations were carried out with fresh cocoa beans, inoculated with 7 different yeast strains. Fermentations were carried out for 7 days (see Materials and Methods), which allowed the pulp around the beans fermented with *Pichia kluyveri* PK-KR1 to liquefy completely. After fermentation, the beans were collected and dried artificially in an oven at 40° C.

Figure 2:
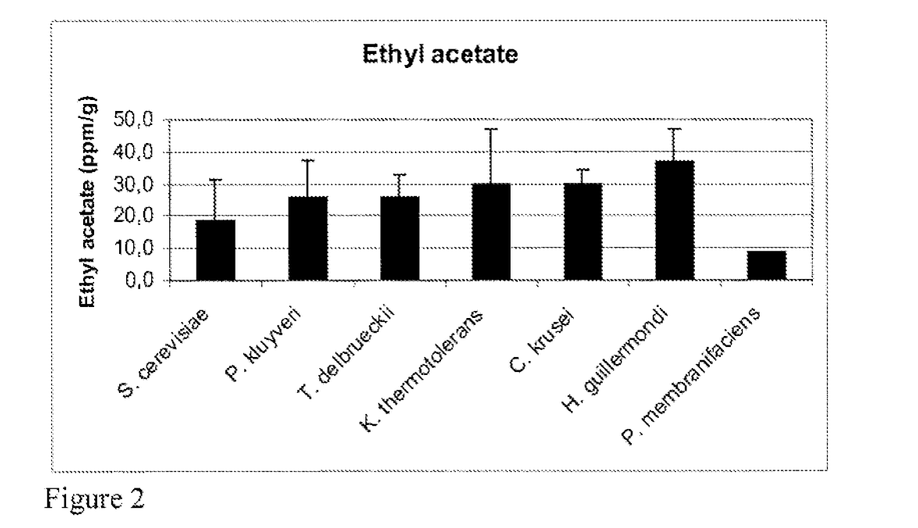
FIG. 2 illustrates ethyl acetate concentrations (in ppm/g) in cocoa nibs, obtained by the fermentation of cocoa beans with 7 different yeast strains.
Figure 3:
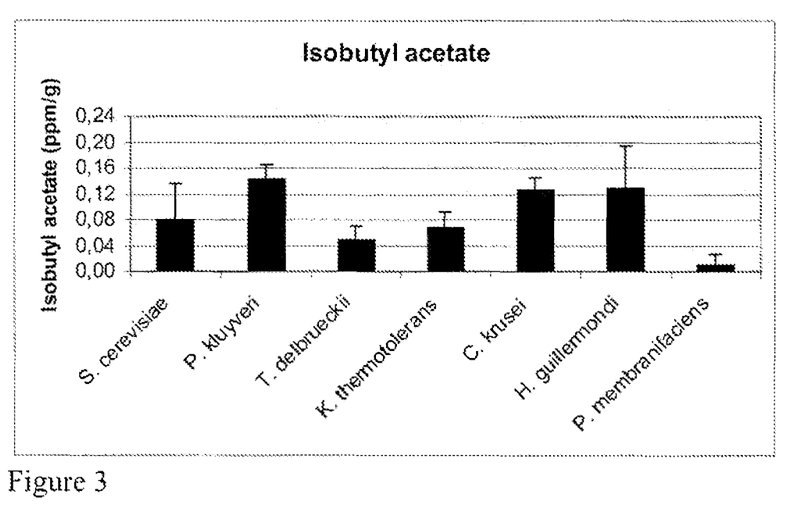
FIG. 3 illustrates isobutyl acetate concentrations (in ppm/g) in cocoa nibs, obtained by the fermentation of cocoa beans with 7 different yeast strains.
Figure 4:
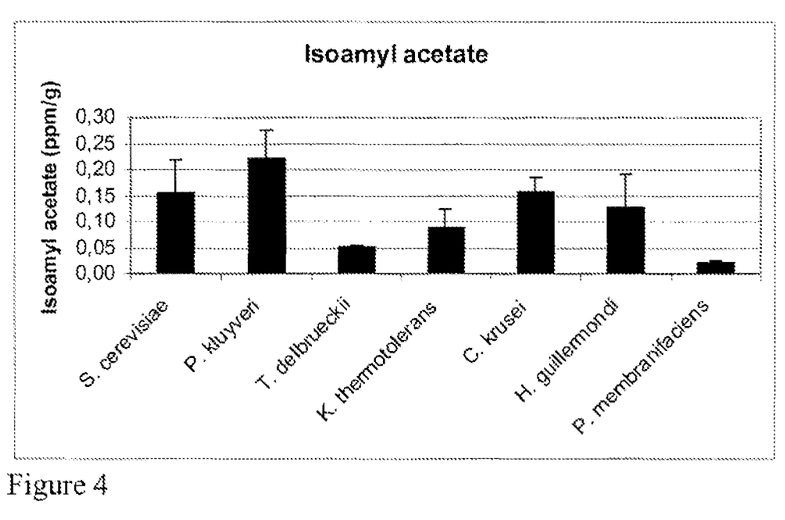
FIG. 4 illustrates isoamyl acetate concentrations (in ppm/g) in cocoa nibs, obtained by the fermentation of cocoa beans with 7 different yeast strains.

Flavor analysis of the fermented and dried cocoa beans was carried out with headspace GC-FID as described in Materials and Methods. Results are depicted in FIG. 1 (aldehydes), FIG. 2-4 (acetate esters), FIG. 5-7 (ethyl esters), and FIG. 8-9 (higher alcohols).

Figure 10:
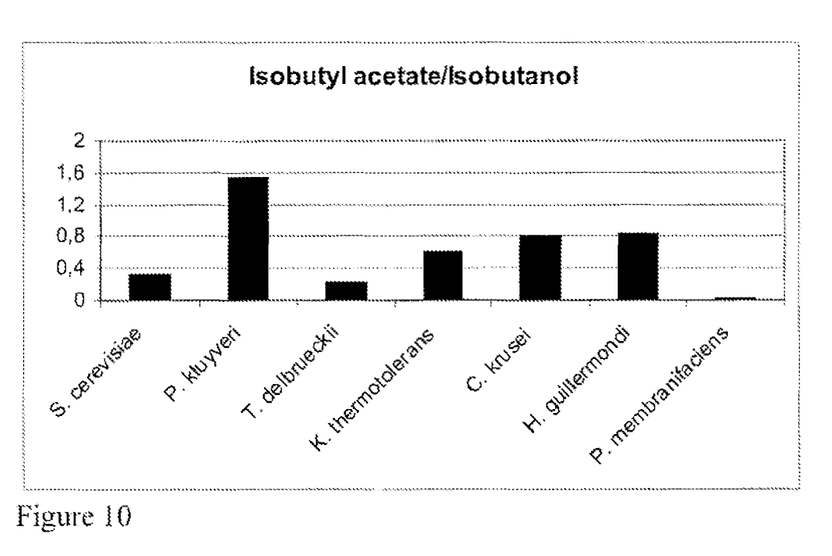
FIG. 10 illustrates ratio of isobutyl acetate/Isobutanol in cocoa nibs, obtained by fermentation of cocoa beans with 7 different yeast strains.
Figure 11:
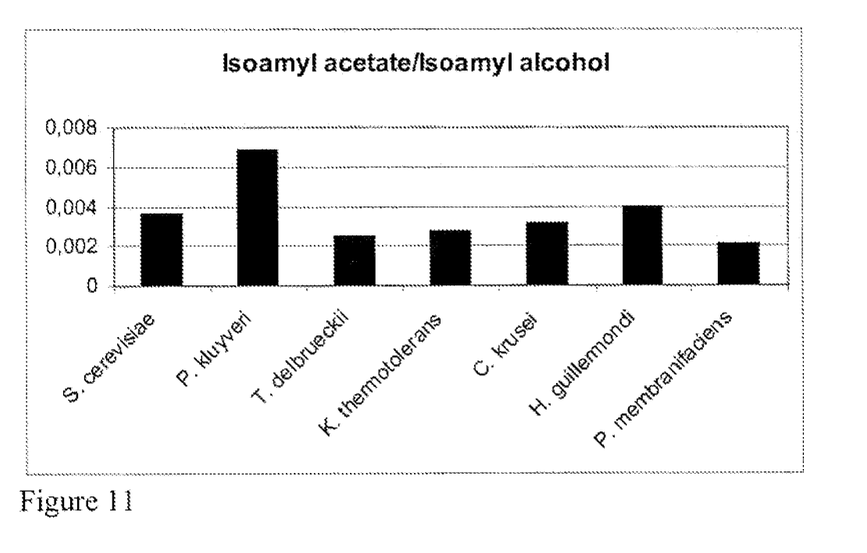
FIG. 11 illustrates ratio of isoamyl acetate/isoamyl alcohol in cocoa nibs, obtained by fermentation of cocoa beans with 7 different yeast strains.

As acetate esters are formed from higher alcohols, the ratio of acetate ester over the respective higher alcohol precursor, gives an idea of the efficiency of the yeast strain to produce a certain ester (see FIG. 10-11). This is specific for a specific condition used. In this case, this is specific for the cocoa bean fermentation.

Discussion

Figure 1:
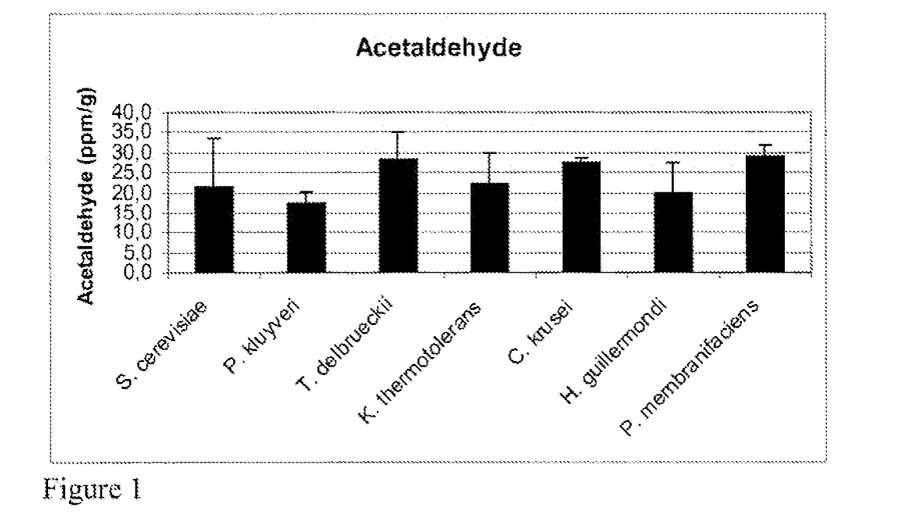
FIG. 1 illustrates acetaldehyde concentrations (In ppm/g) in cocoa nibs, obtained by fermentation of cocoa beans with 7 different yeast strains.

Acetaldehyde concentrations were not statistically different between the cocoa nibs of beans fermented with different yeast strains (see FIG. 1).

The highest flavor differences were found for esters. If we look closer to the acetate ester concentrations, especially the concentration of Isoamyl acetate, which is a desirable fruity flavor compound, was highly increased in the cocoa nibs from cocoa beans fermented with *Pichia kluyveri*, compared to the other yeast strains. Also isobutyl acetate concentration was increased in the cocoa nibs from cocoa beans fermented with *Pichia kluyveri*, compared to the other yeast strains. Ethyl acetate, which is a negative compound at high concentrations because of nail polish flavor, but easily masked by other acetate esters, was increased in the cocoa nibs from cocoa beans fermented with *Hanseniapora guillermondii* and decreased with *Pichia membranifaciens*.

Figure 5:
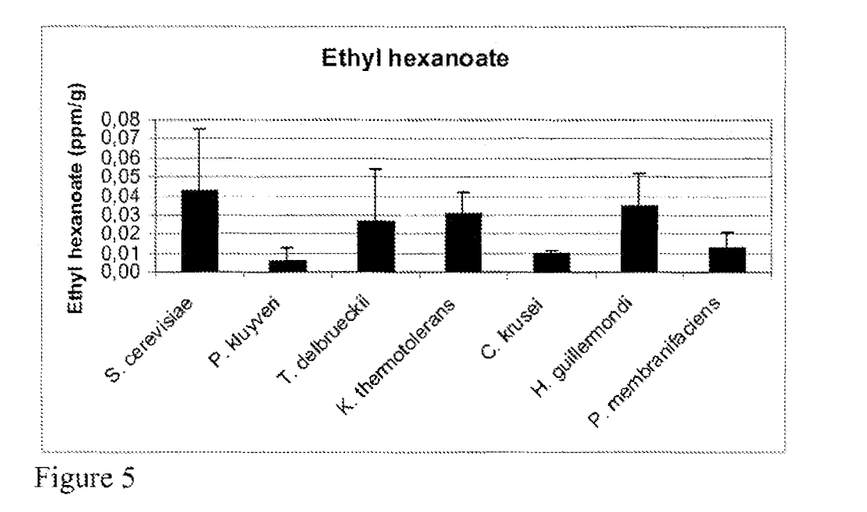
FIG. 5 illustrates ethyl hexanoate concentrations (in ppm/g) in cocoa nibs, obtained by the fermentation of cocoa beans with 7 different yeast strains.
Figure 6:
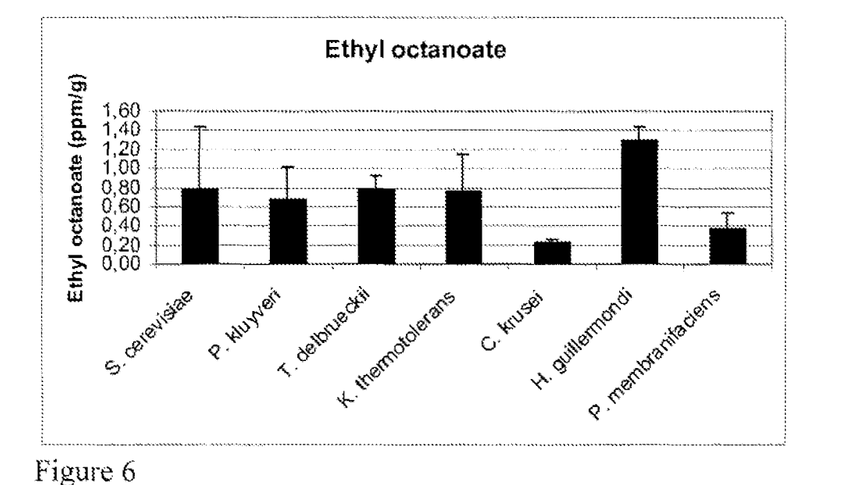
FIG. 6 illustrates ethyl octanoate concentrations (in ppm/g) in cocoa nibs, obtained by the fermentation of cocoa beans with 7 different yeast strains.
Figure 7:
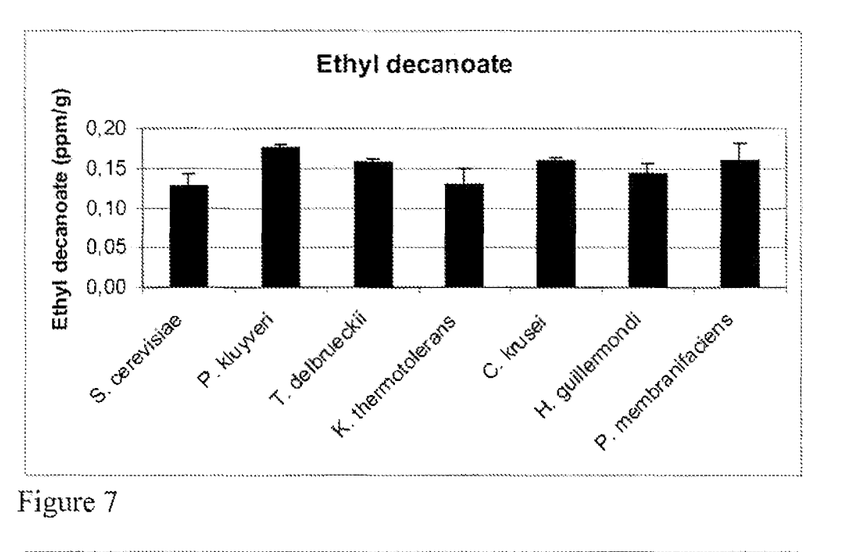
FIG. 7 illustrates ethyl decanoate concentrations (in ppm/g) in cocoa nibs, obtained by the fermentation of cocoa beans with 7 different yeast strains.

The ethyl esters measured were ethyl hexanoate, octanoate and decanoate (FIGS. 5-7). High concentrations of ethyl hexanoate were reached in coco nibs fermented with *Saccharomyces cerevisiae* and *Hanseniapora guillermondii*, while low concentrations were achieved in the fermentations with *Pichia kluyveri* and *Candida krusei*. Ethyl octanoate was found in the highest concentration, compared to ethyl hexanoate and decanoate. Here, the highest level was obtained in the fermentations with *Hanseniapora guillermondii* and the lowest level was found in the fermentation with *Candida krusei*. For ethyl decanoate, no difference was found between all the different yeast strains.

Figure 8:
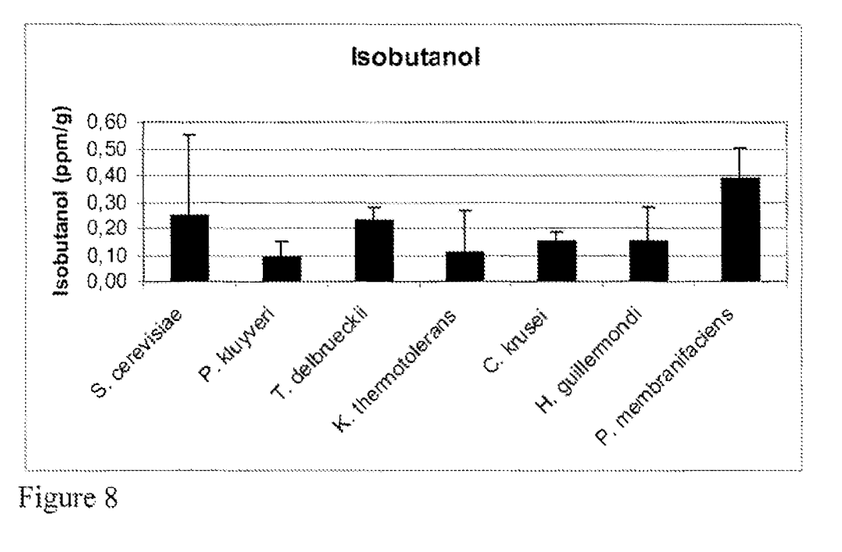
FIG. 8 illustrates isobutanol concentrations (in ppm/g) in cocoa nibs, obtained by the fermentation of cocoa beans with 7 different yeast strains.
Figure 9:
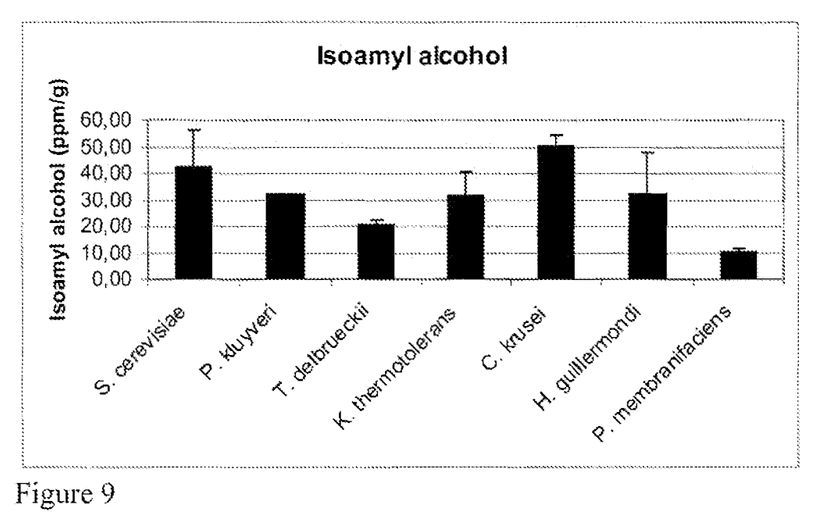
FIG. 9 illustrates isoamyl alcohol concentrations (in ppm/g) in cocoa nibs, obtained by the fermentation of cocoa beans with 7 different yeast strains.

Concentrations of isobutanol reached the highest level in the fermentation with *Hanseniapora guillermondii* and lowest level was reached in the fermentation with *Pichia kluyveri* (FIG. 8). Isoamyl alcohol level was highest in the fermentation with *Candida krusei* and lowest in the fermentation with *Pichia membranifaciens* (FIG. 9).

As acetate esters are formed from higher alcohols as substrate, the ratio of acetate ester over respective higher alcohol precursor is a way to measure the catalytic efficiency of a yeast strain to produce acetate esters and this in a specific condition (FIGS. 10 and 11).

From the complete flavor analysis of all the fermentations, it is clear that *Pichia kluyveri* produces the highest amounts of desirable flavours, i.e. isobutyl and isoamyl acetate. This means that the *Pichia kluyveri* strain has a huge effect on the flavor profile of the cocoa nibs. As remarkable increases were found for the ratio of acetate esters over the respective alcohols for the desirable flavor compounds isoamyl and isobutyl acetate, this shows an enormous potential of using *Pichia kluyveri* as starter culture for cocoa fermentations.

In addition, the *Pichia kluyveri* strain was the only strain able to liquefy the cocoa pulp completely after 7 days of fermentation at 30° C., which is an indication of high pectinolytic activity. On top of that, the liquefaction was much faster, compared to the other strains. This indicates that the *Pichia kluyveri* is very efficient in cocoa fermentation, as the reduction in final cocoa pulp volume improves the final quality (less shell content in the final dried cocoa beans).

Example 2

Production-scale cocoa fermentations have been carried out to support the finding that using a *Pichia kluyveri* starter culture for cocoa fermentations enhance the cocoa quality and flavor.

Materials and Methods

Fermentation Set-Up

A total of 4 fermentations on 'bulk cocoa' have been performed:
1) cocoa fermentation inoculated with *Pichia kluyveri* yeast strain PK-KR1 in duplicate.
2) a non-inoculated spontaneous control cocoa fermentation in duplicate.

The fermentation set-up was carried out in heaps of approximately 100 kg of raw cocoa beans, covered with plastic. The cocoa beans are referred to as 'bulk cocoa', meaning a blend of Trinitarlo, Forastero and Criollo varieties.

Fermentation Protocol

1) Inoculation with yeast strain *Pichia kluyveri* PK-KR1 (PK)

Only *Pichia kluyveri* is inoculated

Protocol

Inoculation of yeast was performed after the cocoa pods were opened and a heap was formed: The cocoa pods were opened and the cocoa beans were removed and put into a basket. The placenta inside the cocoa pod was removed. The cocoa beans were poured onto banana leaves to start forming the heap. A heap of approximately 100 kg was formed.

The yeast was added directly onto the heap of cocoa beans:

A bag of frozen yeast was thawed in water. Once thawed, the yeast slurry from the bag was suspended in water in a 1/1 dilution. The yeast was inoculated at 5 million cells/g cocoa beans, which was equivalent to 500 ml yeast slurry/100 kg beans. The yeast suspension was poured into a watering can. The yeast suspension was spread over the heaps of cocoa beans and mixed well with the beans.

The fermentations were covered with banana leaves and afterwards with plastic foil to protect the cocoa beans against the rain. A thermometer and a pH meter were put into one selected heap to follow temperature and pH constantly.

Sampling

Every day (including a zero time point), samples were taken for yeast and bacteria counting (YGC and GJ5 plating) For the yeast and bacteria cell count, 10 g of cocoa beans was mixed with 90 ml of peptone water in a Stomacher bag. The cocoa beans were washed well in the peptone water and 1 ml of sample was taken from this bag to make serial dilutions. The 1 ml sample was diluted in 9 ml peptone water. Decimal dilutions were made from this bottle and plated on the respective media. Plating was done on GJ5 for lactic acid bacteria and YGC for yeast.

2) Spontaneous Control (SP)

No inoculation of yeast was performed.

Protocol

The cocoa pods were opened and a heap was formed:

The cocoa pods were opened and the cocoa beans were removed and put into a basket. The placenta inside the cocoa pod was removed. The cocoa beans were poured onto banana leaves to start forming the heap. A heap of approximately 100 kg was formed. The fermentations were covered with banana leaves and afterwards with plastic foil to protect the cocoa beans against the rain.

A thermometer and a pH meter were put into one selected heap to follow temperature and pH constantly.

Sampling

Every day (including a zero time point), samples were taken for yeast and bacteria counting (YGC and GJ5 plating)

For the yeast and bacteria cell count, 10 g of cocoa beans was mixed with 90 ml of peptone water in a Stomacher bag. The cocoa beans were washed well in the peptone water and 1 ml of sample was taken from this bag to make serial dilutions. The 1 ml sample was diluted in 9 ml peptone water. Decimal dilutions were made from this bottle and plated on the respective media. Plating was done on GJ5 for lactic acid bacteria and YGC for yeast.

GJ5 is made of grape juice concentrate (77.5 g/L, K V Saft Vallø), yeast extract (22.4 g/L; Bio Springer), Tween® 80 (0.6 g/L; Sigma-Aldrich), $MnSO_4$, $H_2O$ (0.1 g/L; Merck), and agar (15 g/L; SO-BI-GEL) in tap water. YGC is made of yeast extract (5.0 g/L; Oxoid L21), D-glucose-monohydrat (20.0 g/L; Merck), chloramphenicol (0.1 g/L; Fluka) and agar (15 g/L; SO-BI-GEL) in Milli-Q water (Millipore).

Heap Fermentation Information

All fermentations were carried out for 5 days (see Table 1). The weight of every fermentation was around 100 kg (see Table 1). The fermentations were turned (mixed) after 48 and 96 hours in order to have a homogeneous fermentation and to let air into the fermentation.

TABLE 1

Heap weight information

| Fermentation | Weight wet mass (kg) |
|---|---|
| SP_A | 100 |
| SP_B | 106 |
| PK_A | 108 |
| PK_B | 89.5 |

Post Fermentation Processes

After the fermentations were done, the beans were collected and dried under a shed on bamboo mats. The cocoa beans were dried for 8 days, until the moisture content was around 8% (see Table 2). After drying, the cocoa beans were collected and samples were taken for roasting. The roasting conditions are mentioned in Table 3. The roasted samples were used to make cocoa liquor for tasting. Cocoa liquor is made by removing the shells of the cocoa beans and grinding the 'nibs' (inside of cocoa beans) to achieve a cocoa paste-cocoa liquor.

TABLE 2

Drying conditions (sun-drying)

| Fermentation | Drying time (days) | Weight dry cocoa beans (kg) | Moisture content (%) |
|---|---|---|---|
| SP_A | 8 | 38.3 | 8.1 |
| SP_B | 8 | 40.1 | 8.0 |
| PK_A | 8 | 41.0 | 8.0 |
| PK_B | 8 | 34.9 | 7.9 |

TABLE 3

Roasting conditions

| Fermentation | Roasting temperature (° C.) | Roasting time (min) |
|---|---|---|
| SP_A | 130 | 18 |
| SP_B | 130 | 20 |
| PK_A | 130 | 22 |
| PK_B | 130 | 20 |

Results

Yeast and Bacteria Growth

After the end of all cocoa fermentations, all YGC and GJ5 plates were counted to analyse yeast and lactic acid bacteria growth. Results are plotted per fermentation (see FIGS. 12, 13, 14 and 15).

Figure 12:
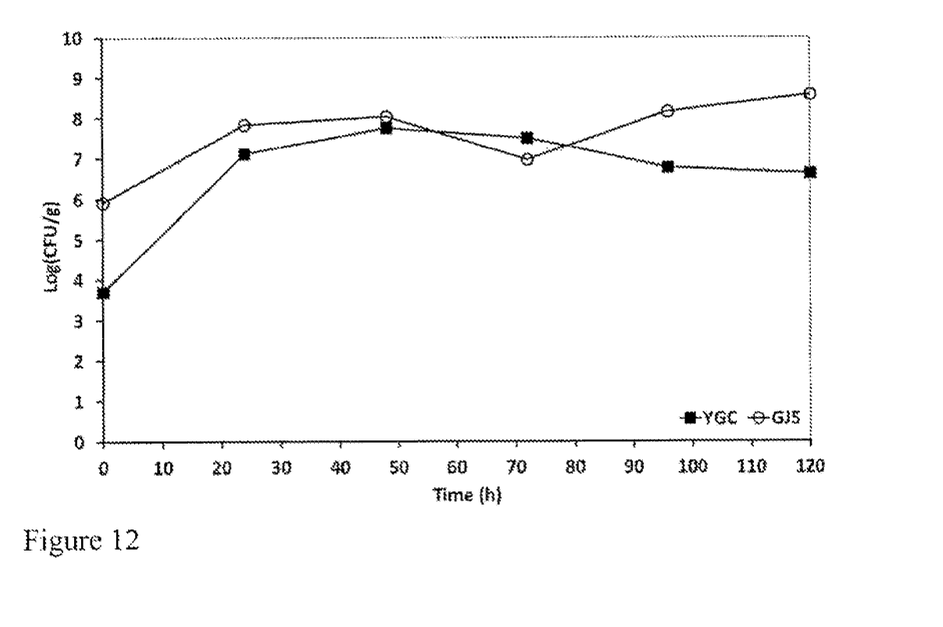
FIG. 12 illustrates yeast (YGC) and lactic acid bacteria (GJ5) cell numbers during spontaneous cocoa fermentation (SP_A).
Figure 13:
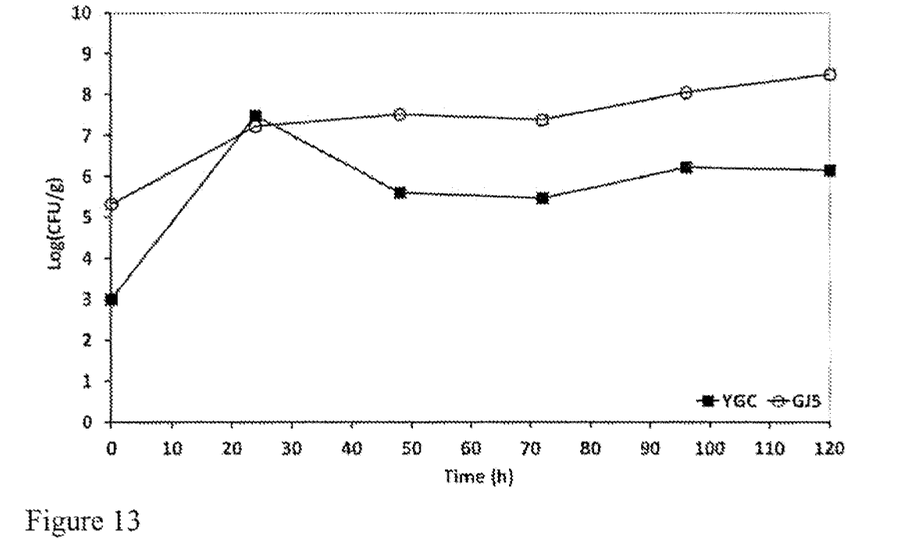
FIG. 13 illustrates yeast (YGC) and lactic acid bacteria (GJ5) cell numbers during spontaneous cocoa fermentation (SP_B).

For the Spontaneous Fermentation (SP_A and B):
  yeast grew to 50 million cells per g, in both duplicates. However, in SP_B, yeast cells dropped in concentration to 1 million cells per ml after the first turning (48 h), while the yeast growth was steadier in SP_A.
  lactic acid bacteria on GJ5 grew to 100 million cells per g in both duplicate fermentations, with a slower start in fermentation B. The lactic acid bacteria stayed at a high concentration until the end of fermentation.

Figure 14:
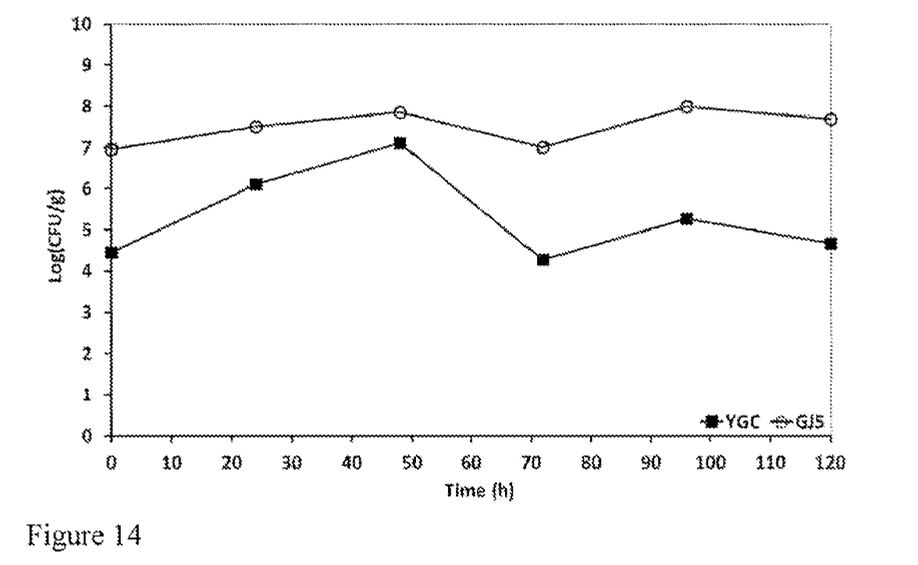
FIG. 14 illustrates yeast (YGC) and lactic acid bacteria (GJ5) cell numbers during inculated cocoa fermentation (PK_A).
Figure 15:
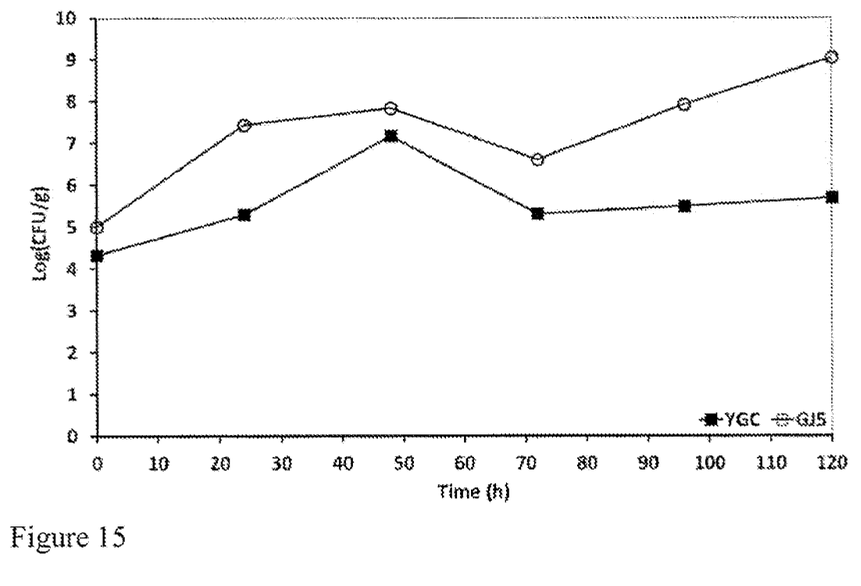
FIG. 15 illustrates yeast (YGC) and lactic acid bacteria (GJ5) cell numbers during inculated cocoa fermentation (PK_B).

For the Fermentation with Inoculation of *Pichia kluyveri* (PK_A and B):
  yeast grew to 10 million cells per g, in both duplicates, and reached the maximum just after turning (48 h). After three days, cell counts dropped to 0.1 million cells per g. *Pichia kluyveri* yeast cells formed the majority of yeast cells on the plates of the first three days.
  lactic acid bacteria on GJ5 followed more or less the same trend as in the spontaneous fermentations.

Tasting of Cocoa Beans

Cocoa liquor was made for all 4 fermentations. The liquor was tasted by a professional taste panel of 9 people and scored on:
  cocoa taste
  bitterness
  astringent
  floral
  fruity
  raw/green
  nutty
  off-flavours The results are given in FIG. 16. The results shown are the average of samples A and B for each fermentation.

Figure 16:
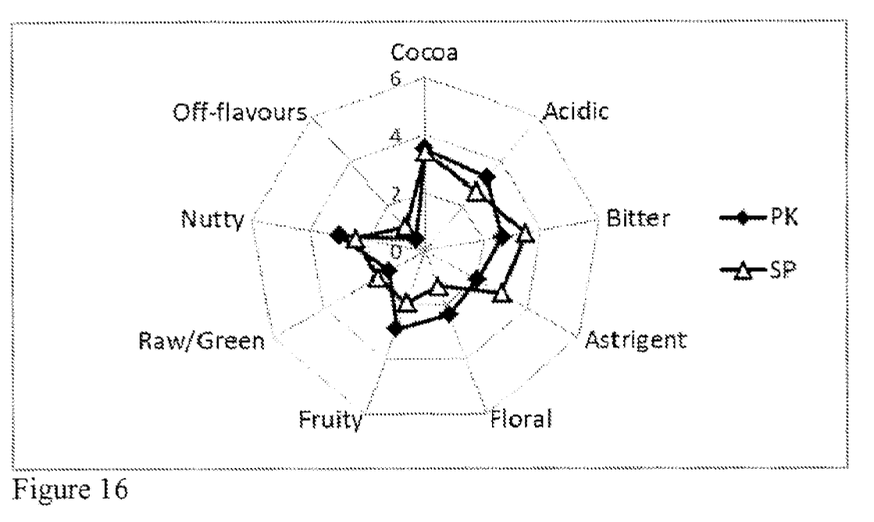
FIG. 16 illustrates flavor descriptive tasting results of cocoa liquor from inoculated (PK) and spontaneous (SP) cocoa bean fermentations.

In general, the taste of the cocoa beans inoculated with *Pichia kluyveri* was perceived as the most cocoa, floral, nutty and fruity compared to cocoa beans from the spontaneous fermentation. The spontaneous fermentation gave cocoa beans with the most bitter and astringent flavor. This fermentation also produced the most cocoa beans with off-flavours. This might be related to mold growth in the spontaneous fermentation.

Figure 17:
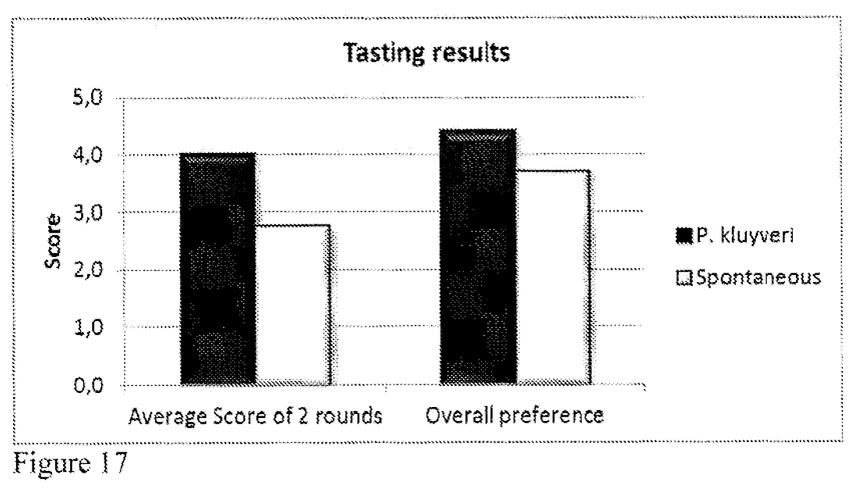
FIG. 17 illustrates scoring and preference of cocoa liquor from inoculated (*P. kluyveri*) and spontaneous cocoa bean fermentation. Maximum score is 5.

After the flavor descriptive session, the taste panel was also asked to give a score and overall preference to the cocoa beans. The results are depicted in FIG. 17. From the overall preference and average score, it was very clear that the fermentation inoculated with *Pichia kluyveri* with the highest score was preferred the most. The spontaneous fermentation was preferred the least.

Deposits

The *Pichia kluyveri* PK-KR1 and PK-KR2 strains were deposited on 24 Aug. 2006 at the National Measurement Institute, 541-65 Clarke Street, South Melbourne, Victoria 3205, Australia, by University of Auckland, School of Biological Sciences, Auckland 1142, New Zealand, and given the accession numbers V06/022711 and V06/022712, respectively, as described in WO 2009/110807 on page 14.

REFERENCES

Schwan, R. F. (1998). Appl. Environ. Microbiol. 64:1477-1483
Schwan, R. F and Wheals, A. E. (2004) Crit. Rev. Food Sci. Nutr. 44:205-221.
Uma, L. J. R., Almeida, M. H., Nout, M. J. R. and Zwletering, M. H. (2011). Crit. Rev. Food Sci. Nutr. 51:731-761.
Afoakwa, E. O., Paterson, A., Fowler, M. and Ryan, A. (2008). Crit. Rev. Food Sd. Nutr. 48; 840-857.
Jespersen, L. (2003) FEMS Yeast Res. 3:191-200.
Leal, G. A., Gomes, L. H., Efraim, P., Tavares, F. C. d. A. and Figueira, A. (2008). FEMS Yeast Res. 8:788-798.
Lefeber, T, Janssens, M., Camu, N. and Vuyst, L. D. (2010). Appl. Environ. Microbiol. 76:7708-7716.
Lefeber, T., Janssens, M, Moens, F., Gobert, W. and De Vuyst, L. (2011). Appl. Environ. Microbiol. published online ahead of print on 29 Jul. 2011.
WO 2007/031186
WO 2011/012680

The invention claimed is:

1. A method for the fermentation of cocoa beans comprising:
   (a) adding at least one *Pichia kluyveri* yeast strain to a plant material comprising beans and/or pulp derived from fruit pods of the species *Theobroma cacao*; and
   (b) fermenting the plant material to obtain fermented cocoa beans, wherein the fermented cocoa beans have a ratio of isobutyl acetate/isobutanol higher than 1 and a ratio of isoamyl acetate/isoamyl alcohol higher than 0.005.

2. The method according to claim 1 further comprising:
   (c) drying the fermented cocoa beans.

3. The method according to claim 1, wherein the *Pichia kluyveri* strain is selected from *Pichia kluyveri* PK-KR1 and *Pichia kluyveri* PK-KR2 as deposited on 24 Aug. 2006 at the National Measurement Institute, 541-65 Clarke Street, South Melbourne, Victoria 3205, Australia, by University of Auckland, School of Biological Sciences, Auckland 1142, New Zealand, under accession numbers V06/022711 and V06/022712, respectively, and mutant and variant strains thereof, wherein the mutant and variant strains thereof have retained or further improved flavoring properties as compared to V06/022711 and V06/022712, respectively.

4. The method according to claim 1, wherein step (a) is carried out at the start of fermentation.

5. The method according to claim 1, wherein the plant material is fermented with the at least one *Pichia kluyveri* strain for at least 12 hours.

6. The method according to claim 1, further comprising adding to the plant material at least one lactic acid bacterial strain.

7. The method according to claim 6, wherein the at least one lactic acid bacterial strain is a *Lactobacillus plantarum* bacterial strain.

8. The method according to claim 6, wherein the at least one lactic acid bacterial strain is a *Lactobacillus paracasei* bacterial strain.

9. Fermented cocoa beans obtained by the method according to claim 1.

10. A method of preparing a cocoa-based product comprising providing fermented cocoa beans obtained by the method according to claim 1 and preparing thereof a cocoa-based product.

11. A cocoa-based product obtained by the method according to claim 10.

12. The method according to claim 1, wherein the fermented cocoa beans have a ratio of isobutyl acetate to isobutanol of greater than 1.2.

13. The method according to claim 1, wherein the fermented cocoa beans have a ratio of isoamyl acetate to isoamyl alcohol of greater than 0.006.

14. The method according to claim 1, wherein the fermented cocoa beans have (i) enhanced fruity flavors, (ii) enhanced floral flavors, and (iii) reduced off-flavors, as compared to fermented cocoa beans produced from comparable cocoa beans by spontaneous fermentation, but without inoculating the cocoa beans with the at least one *Pichia kluyveri* yeast strain.

15. The method according to claim 1, wherein the fermented cocoa beans are of the variety Forastero.

16. The method according to claim 10, wherein the cocoa-based product is selected from chocolate, cocoa powder, and cocoa butter.

* * * * *